(12) United States Patent
Shi et al.

(10) Patent No.: US 8,189,958 B2
(45) Date of Patent: May 29, 2012

(54) METHOD OF FAST IMAGE RECONSTRUCTION

(75) Inventors: Guogua Shi, Chengdu (CN); Xiqi Li, Chengdu (CN); Ling Wei, Chengdu (CN); Yudong Zhang, Chengdu (CN)

(73) Assignee: Institute of Optics and Electronics Chinese Academy of Sciences, Chengdu (CN)

( * ) Notice: Subject to any disclaimer, the term of this patent is extended or adjusted under 35 U.S.C. 154(b) by 544 days.

(21) Appl. No.: 12/538,006

(22) Filed: Aug. 7, 2009

(65) Prior Publication Data

US 2010/0054626 A1 Mar. 4, 2010

(30) Foreign Application Priority Data

Aug. 27, 2008 (CN) .......................... 2008 1 0119131
Jun. 10, 2009 (CN) .......................... 2009 1 0147925

(51) Int. Cl.
G06K 9/36 (2006.01)
G06K 9/32 (2006.01)

(52) U.S. Cl. ........ 382/280; 382/276; 382/282; 382/298; 382/300

(58) Field of Classification Search .................. 382/276, 382/280, 282, 298, 300
See application file for complete search history.

(56) References Cited

FOREIGN PATENT DOCUMENTS

| JP | 62217730 A | 9/1987 |
|---|---|---|
| JP | 2001320409 A | 11/2001 |
| JP | 2003076385 A | 3/2003 |
| JP | 2004252924 A | 9/2004 |
| JP | 2006211127 A | 8/2006 |
| JP | 2007510143 A | 4/2007 |
| WO | 2008082973 A1 | 7/2008 |

OTHER PUBLICATIONS

State Intellectual Property Office of People's Republic of China; Office Action; Chinese Application No. 200910147925.8; Feb. 22, 2012.

*Primary Examiner* — Matthew Bella
*Assistant Examiner* — Jose M Torres
(74) *Attorney, Agent, or Firm* — Michael J. Donohue; Davis Wright Tremaine LLP

(57) ABSTRACT

The present invention provides a method of fast image construction. The wavelength information is extracted in advance based on characteristics of a Fourier domain Optical Coherent Tomography (OCT) system, to obtain a vector of wavelengths which are in a uniform distribution in a wave number space, and thus to obtain a virtual position coefficient of this wavelength vector at a CCD, from which a weight matrix is calculated based on a transfer function for a discrete Fourier transform with zero-padding interpolation. In operation of the system, the interpolation is carried out based on the weight matrix and collected data, or is carried out based on the weight matrix which has been truncated by being subject to windowing and the collected data, to obtain interpolated data satisfying requirements. The method according to the present invention is simple and easy to implement, by which, it is possible to improve the precision and speed of the Fourier domain OCT data process, and thus to improve the capacity of real-time image reconstruction of the Fourier domain OCT system.

9 Claims, 4 Drawing Sheets

METHOD OF FAST IMAGE RECONSTRUCTION

BACKGROUND OF THE INVENTION

1. Field of Invention

The present invention relates to a method of fast image reconstruction, wherein an interpolation with variable interpolation intervals and an interpolation with variable interpolation intervals where windowing is carried out by means of any available window functions, which are novel and applicable to instruments which need interpolation such as Fourier domain Optical Coherent Tomography (OCT), are adopted, in order to achieve fast image reconstruction.

2. Description of Prior Art

In the field of fast image reconstruction, as a novel contact-less optical detection system with high resolution, a Fourier domain Optical Coherent Tomography (OCT) system obtains structure information, Doppler information and polarization information of an object through scanning the object longitudinally by means of optical interference and then though 2-D or 3-D reconstruction. Therefore, such system can find its application in a variety of fields including medical imaging and industrial damage detection. According to the Fourier domain OCT technology, a reference light and a signal light interferes with each other in an optical splitter 3, and then the interference signal undergoes spectrum-division at a diffraction grating 9 and then is focused by a lens 10 onto a linear scanning CCD 11, which converts the analog signal into a digital signal, as shown in FIG. 2. A spectrometer 8 consists of the diffraction grating 9, the lens 10 and the linear scanning CCD 11. Wavelengths collected by the CCD 11, which exit from the grating, are in a linear distribution. However, data reconstruction requires a linear distribution in a K space of the wavelength information, and thus needs interpolation of data. For a Fourier domain OCT system, various types of interpolations are applicable to fast image reconstruction, for example, discrete Fourier transform with zero-padding interpolation, B-spline fitting, direct linear interpolation or the like. However, most Fourier domain OCT systems adopt a combination of the discrete Fourier transform with zero-padding interpolation and the direct linear interpolation. Specifically, N points of data are subject to a discrete Fourier transform to obtain N points of data in a frequency domain, which then are padded with M*N points of zero values at high-frequency points to obtain M*N+N points of data in the frequency domain, which then are subject to an inverse Fourier transform to obtain M*N+N points of data. Here, M is a factor of zero-padding. Finally, N points of interpolated data are obtained by means of linear interpolation. Suppose a vector of data collected by a Fourier domain OCT system through scanning is $\vec{x} = \{x_1, x_2, \ldots, x_N\}$, then the conventional discrete Fourier transform with zero-padding interpolation comprises steps of:

1) carrying out discrete Fourier transform on the data to obtain a new set of data:

$$X_1(i) = \sum_{n=0}^{N-1} x_{n+1} \exp\left(-j\frac{2\pi}{N}in\right);$$

2) carrying out zero-padding interpolation on the new set of data to obtain a set of data padded with zeros at a factor of M:

$$X_2(i) = \begin{cases} X_1(i), & 0 \le i \le \frac{N}{2} - 1 \\ 0, & \text{otherwise} \\ X_1(i - MN), & (M+1)*N - \frac{N}{2} \le i \le (M+1)*N - 1; \end{cases}$$

3) carrying out inverse Fourier transform on the set of data padded with zeroes at the factor M to obtain a set of data which are expanded at a factor of (M+1); and 4) carrying out linear interpolation on the expanded data in accordance with a linear distribution in the K space to obtain interpolated data.

Though such method is simple and well-developed, it has disadvantages such as significant amount of computations, as a result of which requirements of real-time image reconstruction cannot be satisfied, and fixed interpolation intervals and interpolation precision determined by the factor M of zero-padding, as a result of which interpolation intervals cannot be varied as desired. Further, the interpolation precision is degraded due to discrete Fourier transform with zero-padding interpolation followed by linear interpolation. All those limitations strictly restrict the fast image reconstruction application of Fourier domain OCT systems.

SUMMARY OF THE INVENTION

As described above, the existing Fourier domain Optical Coherent Tomography (OCT) technology has disadvantages such as low interpolation precision, low computation speed, and fixed interpolation intervals which cannot be varied as desired. The present invention aims to solve those problems. The present invention provides a method of fast image reconstruction, wherein a novel interpolation is adopted, which has advantages such as high precision, high computation speed, and variable interpolation precision and interpolation intervals. As a result, the computation speed and interpolation precision of a Fourier domain OCT system can be improved efficiently.

According to the present invention, an interpolation with variable interpolation intervals and an interpolation with variable interpolation intervals where windowing is carried out by means of any available window functions are applied to the Fourier domain OCT technology. Specifically, the present invention may be implemented as follows.

(1) Wavelengths which, after being diffracted by the diffraction grating 9 and then passing through the lens 10, are incident on the linear scanning CCD 11 with N points of pixels, are accurately determined by a spectrometer, to obtain a vector $\vec{\lambda}_1 = \{\lambda_1, \lambda_2, \ldots, \lambda_N\}$ of wavelengths which are in an uniform distribution and correspond to the respective pixels of the CCD 11, with a wavelength difference $\Delta\lambda$, an actual position coefficient of the wavelength vector at the CCD 11 being $\text{Index1} = \{n; n=1, 2, \ldots, N\}$.

(2) From the first wavelength $\lambda_1$ and the last wavelength $\lambda_N$, wave numbers corresponding to the first and last pixel points of the CCD 11 can be calculated, based on an equation $k=2\pi/\lambda$, as $k'_1=2\pi/\lambda_1$ and $k'_N=2\pi/\lambda_N$ respectively. By means of $k'_1$ and $k'_N$, a wave number vector which is in a linear distribution and has a length of N can be formed as $$\vec{k}' = \left\{k'_n = k'_1 + \frac{k'_N - k'_1}{N-1} * (n-1); n = 1, 2, \ldots, N\right\}.$$

A corresponding wavelength vector can be calculated, based on an equation $$\lambda = \frac{2\pi}{k},$$

as $$\vec{\lambda}_2 = \left\{\lambda'_n = \frac{2\pi}{k'_n}, n = 1, 2, \ldots, N\right\}.$$

Thus, by means of $\Delta\lambda$, a virtual position coefficient of $\lambda'_n$ corresponding to the respective wave number $k'_n$ at the CCD 11 can be calculated as $$\vec{Index2} = \left\{s_n = \frac{\lambda'_n - \lambda'_1}{\Delta\lambda} + 1; n = 1, 2, \ldots, N\right\}$$

(or otherwise, $$\vec{Index2} = \left\{s_n = \frac{\lambda'_n - \lambda'_1}{\Delta\lambda}; n = 1, 2, \ldots, N\right\}).$$

(3) Due to the fact that the data collected by the CCD 11 are in form of real numbers and that real signals are Hermitian symmetric during a discrete Fourier transform, some points of data may be added at high frequency points. That is, $$X_2(i) = \begin{cases} X_1(i), & 0 \le i \le \frac{N}{2} \\ 0, & \text{otherwise} \\ X_1(i - MN), & (M+1)*N - \frac{N}{2} \le i \le (M+1)*N - 1 \end{cases}$$

Thus, an improved transfer function for the discrete Fourier transform with zero-padding interpolation can be obtained as $$TF(n, s_n) = 1 + \sum_{i=1}^{N/2} \cos\left(\frac{2\pi}{N}i(n - s_n)\right).$$

By substituting different positions n and $s_n$ in order from $\vec{Index1} = \{n; n=1, 2, \ldots, N\}$ and $$\vec{Index2} = \left\{s_n = \frac{\lambda'_n - \lambda'_1}{\Delta\lambda} + 1; n = 1, 2, \ldots, N\right\}$$

(or otherwise, $$\vec{Index2} = \left\{s_n = \frac{\lambda'_n - \lambda'_1}{\Delta\lambda}; n = 1, 2, \ldots, N\right\}$$

to $$TF(n, s_n) = 1 + \sum_{i=1}^{N/2} \cos\left(\frac{2\pi}{N}i(n - s_n)\right),$$

a weight matrix of N*N can be obtained as $H_{N*N}(n, s_n)$. Then, the process on interpolation weights is completed.

(4) The CCD 11 of the Fourier domain OCT system collects a data vector $x = \{x_1, x_2, \ldots, x_N\}$ by longitudinally scanning. This data vector is subject to interpolation, to obtain interpolated data $x' = \{x_{s1}, x_{s2}, \ldots, x_{sN}\}$, based on the following equation $$x'(s_n) = \sum_{n=1}^{N} x_n H_{N*N}(n, s_n).$$

The interpolation process may be truncated by means of any available window functions. An interpolation start position Min and an interpolation end position Max can be obtained from a window length and $$\vec{Index2} = \left\{s_n = \frac{\lambda'_n - \lambda'_1}{\Delta\lambda} + 1; n = 1, 2, \ldots, N\right\}$$

(or otherwise, $$\vec{Index2} = \left\{s_n = \frac{\lambda'_n - \lambda'_1}{\Delta\lambda} + 1; n = 1, 2, \ldots, N\right\}).$$

Then, the original data is subject to interpolation based on the following equation $$x'(s_n) = \sum_{n=Min}^{Max} x_n H_{N*N}(n, s_n) W(n - \text{Min}),$$

where W(*) is a window function for windowing, with a window length of L. As a result, the computation speed of this new interpolation method is improved.

In processing Fourier domain OCT data, any available window functions may be used to truncate the weights. The data of the weights $H_{N*N}(n, s_n)$ are windowed to reduce the length of data to be processed and the amount of data to be processed. Specifically, the calculation is carried out based on the following equation $$x'(s_n) = \sum_{n=Min}^{Max} x_n H_{N*N}(n, s_n) W(n - \text{Min}),$$

where W(*) is any one of available window functions. The interpolation start position Min and the interpolation end position Max are obtained from the window length L and the virtual position coefficient $$\vec{Index2} = \left\{s_n = \frac{\lambda'_n - \lambda'_1}{\Delta\lambda} + 1; n = 1, 2, \ldots, N\right\}$$

(or otherwise, $$\vec{Index2} = \left\{s_n = \frac{\lambda'_n - \lambda'_1}{\Delta\lambda}; n = 1, 2, \ldots, N\right\}).$$

As a result, the computation speed of interpolation with variable interpolation intervals is improved, and the weights can be stored in a computer and thus are easy to be called during operation so as to avoid repeated calculations.

Further, based on the law of conservation of energy during the Fourier transform, the Fourier transform with zero-padding interpolation may be modified as follows:

$$X_2(i) = \begin{cases} X_1(i), & 0 \leq i \leq \frac{N}{2} - 1 \\ \frac{1}{\sqrt{2}} X_1(i), & i = \frac{N}{2} \\ 0, & \text{otherwise} \\ \frac{1}{\sqrt{2}} X_1(i), & i = (M+1)*N - \frac{N}{2} \\ X_1(i - MN), & (M+1)*N - \frac{N}{2} < i \leq (M+1)*N - 1 \end{cases}$$

In this case, the transfer function becomes $$TF(n, s_n) = 1 + \sum_{i=1}^{N/2} \cos\left(\frac{2\pi}{N} i(n - s_n)\right) + (\sqrt{2} - 2)\cos(\pi(s_n - n)).$$

And thus, the corresponding weight matrix $H_{N*N}(n,s_n)$ may be obtained.

Furthermore, based on the equal sums during the Fourier transform, the Fourier transform with zero-padding interpolation may be modified as follows:

$$X_2(i) = \begin{cases} X_1(i), & 0 \leq i \leq \frac{N}{2} - 1 \\ \frac{1}{2} X_1(i), & i = \frac{N}{2} \\ 0, & \text{otherwise} \\ \frac{1}{2} X_1(i), & i = (M+1)*N - \frac{N}{2} \\ X_1(i - MN), & (M+1)*N - \frac{N}{2} < i \leq (M+1)*N - 1 \end{cases}$$

In this case, the transfer function becomes $$TF(n, s_n) = 1 + \sum_{i=1}^{N/2} \cos\left(\frac{2\pi}{N} i(n - s_n)\right) - \cos(\pi(s_n - n)).$$

And thus, the corresponding weight matrix $H_{N*N}(n,s_n)$ may be obtained.

The present invention has the following advantages as compared with the prior art.

1. The information on the wavelengths and wave numbers may be extracted in advance to construct the wavelength vector in nonlinear distribution in the K space and the virtual position coefficient vector corresponding to the pixel points of this wavelength vector at the CCD 11, from which the weight matrix $H_{N*N}(n,s_n)$ is calculated based on the transfer function. For the conventional discrete Fourier transform with zero-padding interpolation, the precision is fixed by the zero-padding factor M, and thus can only reach a position precision of 1/(M+1). However, according to the present invention, since the position of the virtual position coefficient $s_n$ is not fixed by the zero-padding factor M for the conventional Fourier transform with zero-padding interpolation and thus may be any real number within the data precision of the computer, it is possible to achieve variable interpolation precision and interpolation intervals.

2. The weight matrix may be truncated by being subject to windowing by means of any available window functions, and may be stored in the computer for convenience of being called during operation so as to avoid repeated calculations. For the conventional discrete Fourier transform with zero-padding interpolation, there are one fast Fourier transform for N points and one fast Fourier transform for M*N+N points, and thus it needs $$\frac{N}{2} \log_2(N) + \frac{(M+1)*N}{2} \log_2((M+1)*N)$$

numbers of complex multiplications. However, according to the present invention, it only needs N*L numbers of real multiplications, wherein N indicates the pixel points of the CCD 11, and L indicates the window length of the window function. As a result, it is possible to improve the computation speed of the interpolation and to improve the real-time process capacity of the discrete Fourier domain OCT system, and thus it is possible to achieve fast image reconstruction.

DETAILED DESCRIPTION OF PREFERRED EMBODIMENTS

Figure 1:
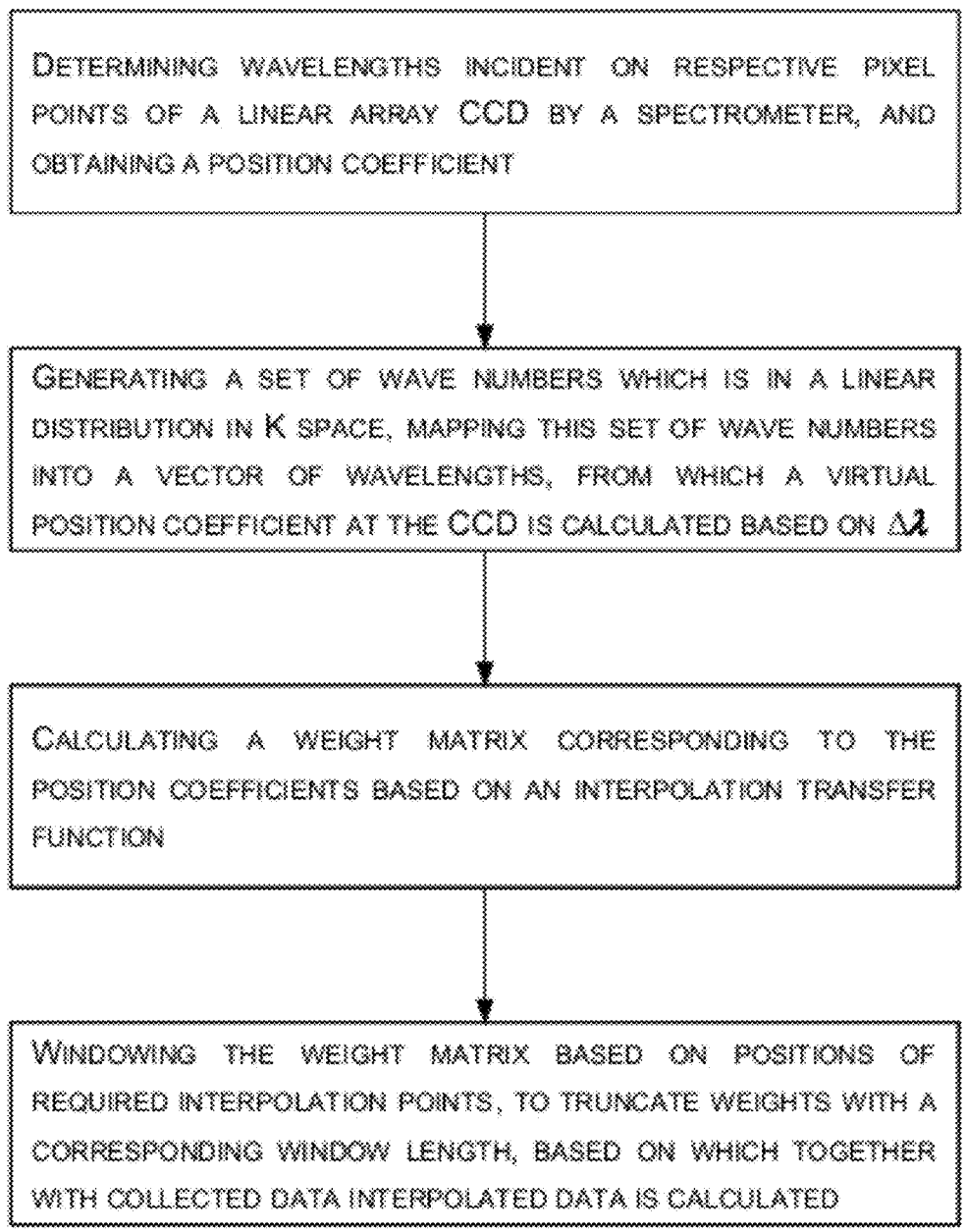
FIG. 1 is a flow chart showing an interpolation of a Fourier domain Optical Coherent Tomography (OCT) system.

The present invention is described in detail hereinafter in conjunction with embodiments thereof and the drawings. According to an embodiment, a Fourier domain Optical Coherent Tomography (OCT) system collects data, which then is subject to interpolation. An operation flow of this system is shown in FIG. 1, which is described in detail in the following.

Figure 2:
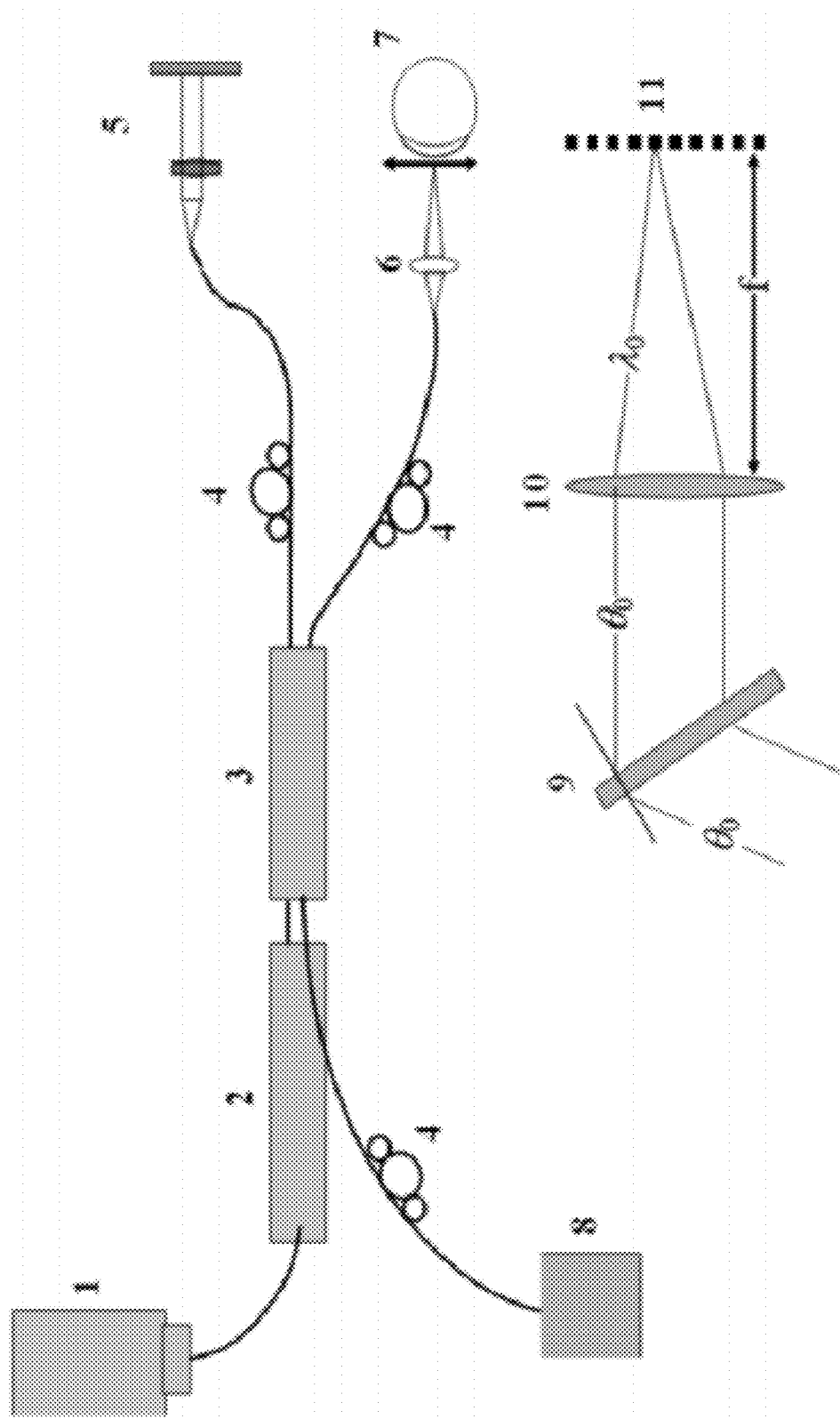
FIG. 2 is a schematic view showing a structure of a Fourier domain OCT system, wherein 1 indicates a light source, 2 indicates an optical isolator, 3 indicates an optical splitter, 4 indicates a polarization controller, 5 indicates a PZT converter, 6 indicates a scan controller, 7 indicates a sample object, 8 indicates a spectrometer, 9 indicates a diffraction grating, 10 indicates a lens, and 11 indicates a linear scanning CCD.

(1) Wavelengths incident on the CCD 11 are accurately determined by the spectrometer shown in FIG. 2. Here, the center wavelength is 849.72 nm, and the spectrum resolution is $\Delta\lambda=0.0674$ nm. The number of pixels of the linear scanning CCD 11 is N=2048, and the wavelengths at the first and last pixel points of the CCD 11 are $\lambda_1=780.7024$ nm and $\lambda_N=918.6702$ nm respectively. A position coefficients of the respective wavelengths at the CCD 11 are $\vec{Index1}=\{n; n=1, 2, \ldots, N\}$.

(2) Two wave numbers corresponding to the first and last pixel points of the CCD 11 can be calculated, based on $$k = \frac{2\pi}{\lambda}, \text{ as } k_1' = \frac{2\pi}{\lambda_1} \text{ and } k_N' = \frac{2\pi}{\lambda_N}$$

respectively. Let a wave number vector which is in a linear distribution in the K space be $$\vec{k}' = \left\{ k_n' = k_1' + \frac{k_N' - k_1'}{N-1} * (n-1); n = 1, 2, \ldots, N \right\}.$$

From this wave number vector which is in a linear distribution in the K space, a set of wavelengths $\lambda' = \{\lambda_1', \lambda_2', \ldots,$ $\lambda'_N\}$ which are not evenly distributed, can be obtained, based on the equation $$\lambda_n = \frac{2\pi}{k_n}.$$

Obviously, $\lambda_1 = \lambda'_1$ and $\lambda_N = \lambda'_N$. Then, a virtual position coefficient of the wavelengths $\lambda' = \{\lambda'_1, \lambda'_2, \ldots, \lambda'_N\}$ at the CCD 11 can be calculated, based on the equation $$s_n = \frac{\lambda'_n - \lambda'_1}{\Delta\lambda} + 1,$$

as $$\vec{\text{Index2}} = \left\{ s_n = \frac{\lambda'_n - \lambda'_1}{\Delta\lambda} + 1; n = 1, 2, \ldots, N \right\}.$$

Alternatively, the above equation of $s_n$ may be $$s_n = \frac{\lambda'_n - \lambda'_1}{\Delta\lambda},$$

which has no effect on the final result. In this case, the virtual position coefficients of the wavelengths $\lambda' = \{\lambda'_1, \lambda'_2, \ldots, \lambda'_N\}$ at the CCD 11 can be calculated as $$\vec{\text{Index2}} = \left\{ s_n = \frac{\lambda'_n - \lambda'_1}{\Delta\lambda}; n = 1, 2, \ldots, N \right\}.$$

Hereinafter, in order to explain the invention in a simple and clear manner, the description is made with respect to the case where the first calculation equation of $s_n$ is adopted. However, this does not exclude the use of the second calculation equation of $s_n$. In fact, the present invention may also be implemented through use of various other calculation equations.

(3) By extracting respective n and $s_n$ in order, from the position coefficient vector of the actual wavelengths at the CCD 11

$$\vec{\text{Index1}} = \{n; n=1, 2, \ldots, N\} \text{ and}$$

the virtual position coefficient vector at the CCD 11

$$\vec{\text{Index2}} = \left\{ s_n = \frac{\lambda'_n - \lambda'_1}{\Delta\lambda} + 1; n = 1, 2, \ldots, N \right\},$$

a weight matrix $H_{N*N}(n, s_n)$ can be obtained based on a transfer function $$TF(n, s_n) = 1 + \sum_{i=1}^{N/2} \cos\left(\frac{2\pi}{N} i (n - s_n)\right).$$

(4) Suppose a set of interference signal data collected by the CCD 11 of the Fourier OCT system shown in FIG. 2 is $x = \{x_1, x_2, \ldots, x_N\}$. The weights are truncated by means of a Blackman window function $$(W(l) = 0.42 + 0.5 * \cos\left(\frac{2\pi l}{L}\right) + 0.08 * \cos\left(\frac{4\pi l}{L}\right),$$

wherein $l \in [0, L-1]$) with a window length $L=11$. And then interpolated data is obtained by means of interpolation equation. Specifically, the calculation is carried out as follows:

$$x'(s_n) = \sum_{n=Min}^{Max} x_n H_{N*N}(n, s_n) W(n - \text{Min}),$$

where $s_n$ is given by $$\vec{\text{Index2}} = \left\{ s_n = \frac{\lambda'_n - \lambda'_1}{\Delta\lambda} + 1; n = 1, 2, \ldots, N \right\},$$

$$\text{Max} = s_n + \frac{L-1}{2},$$

and $$\text{Min} = s_n - \frac{L-1}{2}.$$

(5) The data collected by the CCD 11 of the Fourier domain OCT system is subject to interpolation by repeating step (3), and the respective interpolated data $x'(s)$ is subject to discrete Fourier transform to obtain $X'(s)$. Let a contrast be Contrast=6 and a brightness bias be Brightness_Bias=−82. The respective points of $X'(s)$ are subject to a logarithmic operation to obtain a gradation value Intensity of the image. Specifically, the operation is carried out as follows:

Intensity=Contrast*(10*log 10($X'(s)$)+Brightness_Bias))+255.

Figure 4:
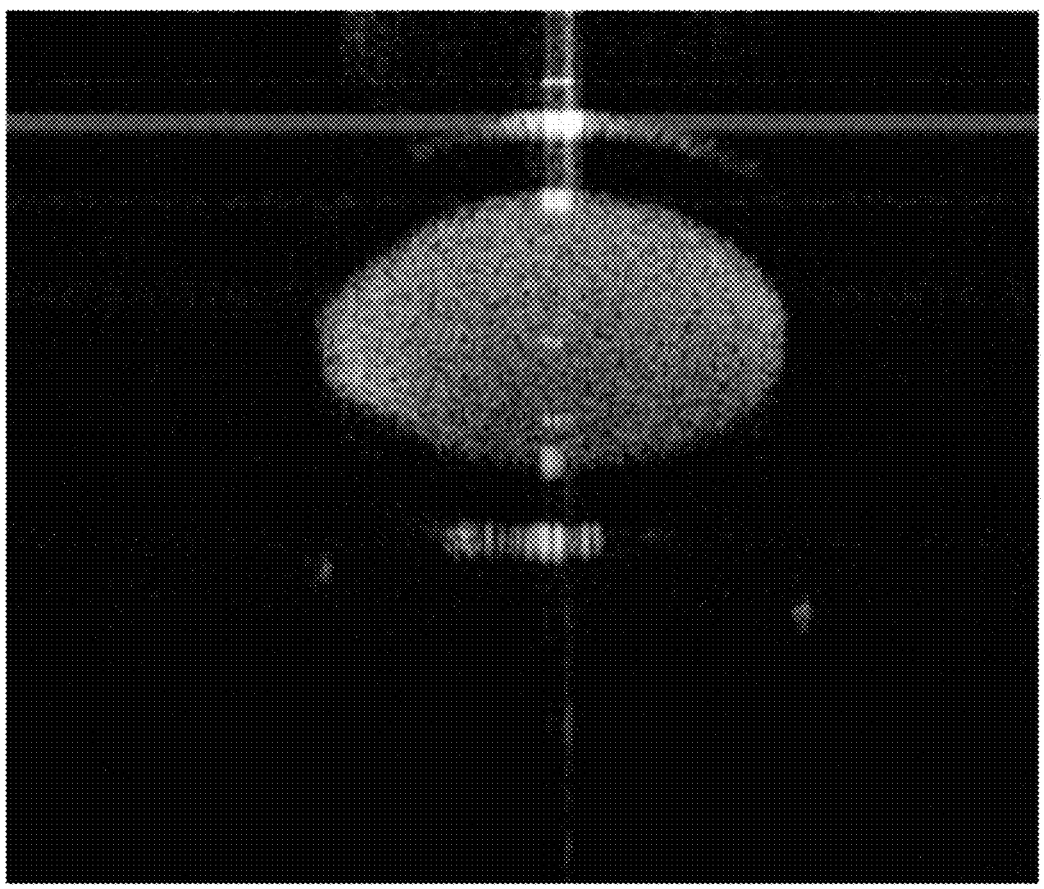
FIG. 4 is a schematic view showing a 2-D image reconstruction.

The calculated gradation value needs to be truncated, wherein a value smaller than 0 should be assigned 0 and a value greater than 255 should be assigned 255. As a result, the gradation value falls into a range of [0, 255], which conforms to a gradation output range of a computer image. A scan controller 6 controls repeated linear scan on a sample object 7, and carries out interpolation and mapping on the interference signal data collected by the CCD 11 to reconstruct a 2-D or 3-D image. FIG. 4 shows an example of a reconstructed 2-D image.

Figure 3:
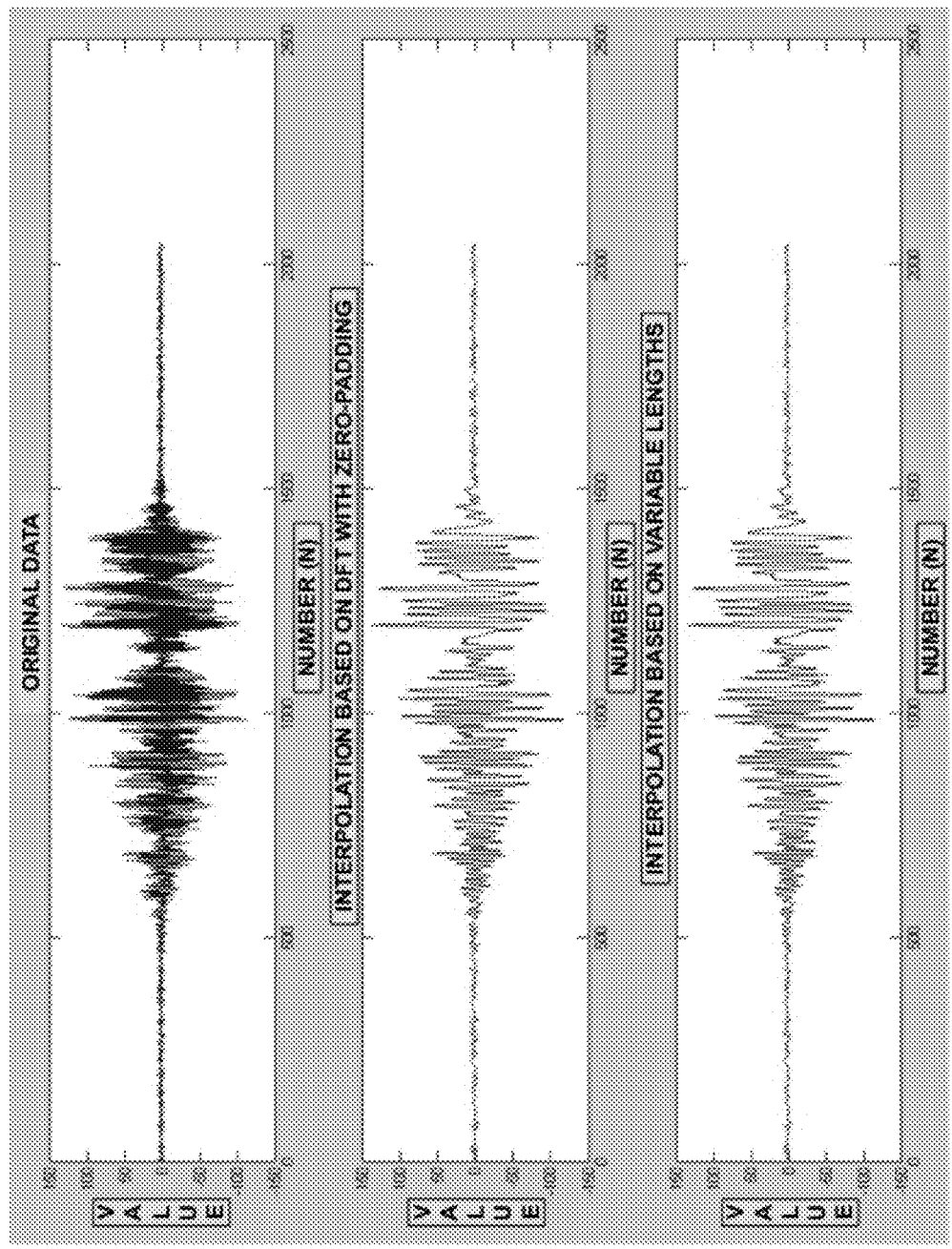
FIG. 3 is a schematic view showing comparative examples of interpolations.

The conventional discrete Fourier transform with zero-padding interpolation is carried out as a comparative example to the present invention. In the experiment, a set of data collected by linear scanning is extracted by a factor of 4, and then is subject to interpolation. The interpolated data is shown in FIG. 3, and after being subtracted from the original data, has a mean value of 0.1409 with a variance of 0.2524 for the novel method proposed by the invention while has a mean value of 0.1448 with a variance of 0.2564 for the conventional discrete Fourier transform with zero-padding interpolation. Thus, the interpolation based on variable intervals according to the present invention is better in terms of mean value and variance. An object is scanned by the Fourier domain OCT system to collect 2048*300 points of data, which are in turn processed to reconstruct the image. The reconstructed image is shown in FIG. 4. Under an operation environment where a CPU is Conroe™ Q9300 and a memory is of 4 GB size, the operation time is reduced from 9 seconds, which it would take by means of the conventional method, to 400 microseconds, which it will take by means of the method according to the present invention. That is, the processing speed is significantly improved.

Based on the law of conservation of energy during the Fourier transform, the Fourier transform with zero-padding interpolation may be modified as follows:

$$X_2(i) = \begin{cases} X_1(i), & 0 \le i \le \frac{N}{2} - 1 \\ \frac{1}{\sqrt{2}} X_1(i), & i = \frac{N}{2} \\ 0, & \text{otherwise} \\ \frac{1}{\sqrt{2}} X_1(i), & i = (M+1)*N - \frac{N}{2} \\ X_1(i - MN), & (M+1)*N - \frac{N}{2} < i \le (M+1)*N - 1 \end{cases}$$

In this case, the transfer function becomes $$TF(n, s_n) = 1 + \sum_{i=1}^{N/2} \cos\left(\frac{2\pi}{N} i(n - s_n)\right) + (\sqrt{2} - 2)\cos(\pi(s_n - n)).$$

And thus, the corresponding weight matrix $H_{N*N}(n, s_n)$ may be obtained.

Alternatively, based on the equal sums during the Fourier transform, the Fourier transform with zero-padding interpolation may be modified as follows:

$$X_2(i) = \begin{cases} X_1(i), & 0 \le i \le \frac{N}{2} - 1 \\ \frac{1}{2} X_1(i), & i = \frac{N}{2} \\ 0, & \text{otherwise} \\ \frac{1}{2} X_1(i), & i = (M+1)^*N - \frac{N}{2} \\ X_1(i - MN), & (M+1)^*N - \frac{N}{2} < i \le (M+1)^*N - 1 \end{cases}$$

In this case, the transfer function becomes $$TF(n, s_n) = 1 + \sum_{i=1}^{N/2} \cos\left(\frac{2\pi}{N} i(n - s_n)\right) - \cos(\pi(s_n - n)).$$

And thus, the corresponding weight matrix $H_{N*N}(n, s_n)$ may be obtained.

Though the present invention has already been shown and described with reference to the embodiments thereof, it is to be understood that various changes may be made in forms and specifics without departing from the scope and the spirit of the present invention which is defined by the appended claims.

What is claimed is:

1. A method of fast image reconstruction, comprising steps of:
   determining wavelengths, which, after being diffracted by a diffracting grating (9) and then passing through a lens (10), are incident on a linear scanning CCD (11) with N points of pixels, to obtain a vector $\vec{\lambda}_1 = \{\lambda_1, \lambda_2, \ldots \lambda_N\}$ of wavelengths which are in an uniform distribution in a wavelength space, with a wavelength difference $\Delta\lambda$, an actual position coefficient of the wavelength vector at the CCD (11) being $\text{In}\vec{d}\text{ex1} = \{=1, 2, \ldots, N\}$;
   converting a vector of wave numbers, which are uniformly distributed in a wave number space between a wave number corresponding to the shortest wavelength $\lambda_1$ and a wave number corresponding to the longest wavelength $\lambda_N$, into a vector $\vec{\lambda}_2 = \{\lambda_1', \lambda_2', \ldots, \lambda_N'\}$ of wavelengths which are not in an uniform distribution in the wavelength space, and calculating a virtual position coefficient $\text{In}\vec{d}\text{ex2} = \{s_n; n=1, 2, \ldots, N\}$ of the wavelength vector $\vec{\lambda}_2$ at the CCD (11) based on the wavelength difference $\Delta\lambda$;
   based on a transfer function $TF(n, s_n)$ for zero-padding interpolation, deriving a N*N weight matrix $H_{N*N}(n, s_n)$ from $\text{In}\vec{d}\text{edx1} = \{n; n=1, 2, \ldots N\}$ and $\text{In}\vec{d}\text{ex2} = \{s_n; n=1, 2, \ldots, N\}$;
   upon collecting a data vector $x = \{x_1, x_2, \ldots, x_N\}$ by the CCD (11), carrying out interpolation on the data vector $x = \{x_1, x_2, \ldots, x_N\}$ by means of the weight matrix $H_{N*N}(n, s_n)$ to obtain interpolated data $x'(s_n) = \{x_{s1}', x_{s2}', \ldots, x_{sN}'\}$; and
   carrying out a discrete Fourier transform on the interpolated data $x'(s_n)\{x_{s1}', x_{s2}', \ldots, x_{sN}'\}$, for image reconstruction.

2. The method of fast image reconstruction according to claim 1, wherein the transfer function for zero-padding interpolation is based on the following equation $$TF(n, s_n) = 1 + \sum_{i=1}^{N/2} \cos\left(\frac{2\pi}{N} i(n - s_n)\right).$$

3. The method of fast image reconstruction according to claim 1, wherein the transfer function for zero-padding interpolation is based on the following equation $$TF(n, s_n) = 1 + \sum_{i=1}^{N/2} \cos\left(\frac{2\pi}{N} i(n - s_n)\right) + (\sqrt{2} - 2)\cos(\pi(s_n - n)).$$

4. The method of fast image reconstruction according to claim 1, wherein the transfer function for zero-padding interpolation is based on the following equation $$TF(n, s_n) = 1 + \sum_{i=1}^{N/2} \cos\left(\frac{2\pi}{N} i(n - s_n)\right) - \cos(\pi(s_n - n)).$$

5. The method of fast image reconstruction according to claim 1, wherein the virtual position coefficient $\text{Index2} = \{s_n; n=1, 2, \ldots, N\}$ is based on the following equation $$s_n = \frac{\lambda_n' - \lambda_1'}{\Delta\lambda} + 1.$$

6. The method of fast image reconstruction according to claim 1, wherein the virtual position coefficient Index2=$\{s_n; n=1, 2, \ldots, N\}$ is based on the following equation $$s_n = \frac{\lambda'_n - \lambda'_1}{\Delta\lambda}.$$

7. The method of fast image reconstruction according to claim 1, wherein the weight matrix $H_{N*N}(n,s_n)$ is truncated by being subject to windowing based on a window function, and the interpolation is carried out on the data vector $x=\{x_1, x_2, \ldots, x_N\}$ by means of the truncated weight matrix.

8. The method of fast image reconstruction according to claim 1, wherein the interpolation on the data vector $x=\{x_1, x_2, \ldots, x_N\}$ is based on the following equation $$x'(s_n) = \sum_{n=Min}^{Max} x_n H_{N*N}(n, s_n) W(n - Min),$$

wherein W(*) is the window function, and values of Max and Min are determined by a window length of the window function and respective virtual positions together.

9. The method of fast image reconstruction according to claim 1, wherein the discrete Fourier transform is carried out on the interpolated data $x'(s_n)=\{x_{s1}', x_{s2}', \ldots, x_{sN}'\}$ to obtain intensity relative data X'(s), and the image reconstruction is carried out based on the following equation Intensity=Contrast*(10*log 10(X'(s)+Brightness_Bias))+255, wherein Intensity indicates a gradation vale, Contrast indicates a contrast, and Brightness_Bias indicates a brightness bias, and if the calculated gradation value Intensity is smaller than 0, then a value of 0 is assigned to Intensity; and if the calculated gradation value Intensity is greater than 255, then a value of 255 is assigned to Intensity.

* * * * *